US008168948B2

(12) United States Patent
Botman et al.

(10) Patent No.: US 8,168,948 B2
(45) Date of Patent: May 1, 2012

(54) METHOD OF MACHINING A WORK PIECE WITH A FOCUSED PARTICLE BEAM

(75) Inventors: Aurélien Philippe Jean Maclou Botman, Hillsboro, OR (US); Bert Henning Freitag, Eindhoven (NL); Johannes Jacobus Lambertus Mulders, Eindhoven (NL)

(73) Assignee: FEI Company, Hillsboro, OR (US)

( * ) Notice: Subject to any disclaimer, the term of this patent is extended or adjusted under 35 U.S.C. 154(b) by 217 days.

(21) Appl. No.: 12/537,841

(22) Filed: Aug. 7, 2009

(65) Prior Publication Data

US 2010/0032567 A1 Feb. 11, 2010

(30) Foreign Application Priority Data

Aug. 7, 2008 (EP) .................................... 08162003

(51) Int. Cl.
*G01N 23/00* (2006.01)
(52) U.S. Cl. ...... 250/307; 250/306; 250/309; 250/492.1
(58) Field of Classification Search .................. 250/306, 250/307, 309, 310, 311, 492.1, 492.2, 492.21, 250/492.3
See application file for complete search history.

(56) References Cited

U.S. PATENT DOCUMENTS

| | | | |
|---|---|---|---|
| 5,270,552 A | 12/1993 | Ohnishi et al. | |
| 5,312,519 A | 5/1994 | Sakai et al. | |
| 5,811,819 A * | 9/1998 | Ohshima et al. | 250/423 R |
| 6,570,170 B2 | 5/2003 | Moore | |
| 7,002,152 B2 | 2/2006 | Grunewald | |
| 7,675,049 B2 | 3/2010 | Schmidt et al. | |
| 2003/0107005 A1* | 6/2003 | Yagi et al. | 250/372 |
| 2007/0085006 A1* | 4/2007 | Motoki | 250/310 |
| 2007/0158566 A1 | 7/2007 | Ikeda | |
| 2008/0102224 A1 | 5/2008 | Blackwood et al. | |

FOREIGN PATENT DOCUMENTS

| | | |
|---|---|---|
| EP | 1956634 | 8/2008 |
| WO | 2008051937 | 5/2005 |
| WO | 2008049133 | 4/2008 |

OTHER PUBLICATIONS

Ragan et al.,R., "Platinum Passivation of Self-Assembled Erbium Disilicide Nanowire Arrays on Si(001)," Applied Physics A, Materials Science & Processing, Mar. 2005, pp. 1339-1342, XP019336701, vol. 80.
Bozo et al., F., "Reaction of Si(100) with NH3: Rate Limiting Steps and Reactivity Enhancement via Electronic Excitation," Physical Review Letters, Sep. 1986, pp. 1185-1188, XP0025177, vol. 57, No. 9.

* cited by examiner

*Primary Examiner* — Michael Maskell
*Assistant Examiner* — Hanway Chang
(74) *Attorney, Agent, or Firm* — Scheinberg & Griner, LLP; Michael O. Scheinberg; David Griner

(57) ABSTRACT

The invention relates to a method for producing high-quality samples for e.g. TEM inspection. When thinning samples with e.g. a Focused Ion Beam apparatus (FIB), the sample often oxidizes when taken from the FIB due to the exposure to air. This results in low-quality samples, that may be unfit for further analysis. By forming a passivation layer, preferably a hydrogen passivation layer, on the sample in situ, that is: before taking the sample from the FIB, high quality TEM samples can be produced.

24 Claims, 3 Drawing Sheets

METHOD OF MACHINING A WORK PIECE WITH A FOCUSED PARTICLE BEAM

CROSS REFERENCE TO RELATED APPLICATIONS

Not Applicable

STATEMENT REGARDING FEDERALLY SPONSORED RESEARCH

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The invention relates to a method of machining a work piece with a focused particle beam to form a sample, comprising:
Inserting the work piece in a particle-optical apparatus,
Machining the work piece to form the sample by exposing the work piece to a focused particle beam,
Removing the sample from the particle-optical apparatus, 2. Description of Related Art For the inspection of samples, e.g. samples taken from a semiconductor wafer, in a Transmission Electron Microscope (TEM) samples with a thickness of less than 100 nm and preferably less than 50 nm, are routinely used.

U.S. Pat. No. 5,270,552 discloses forming samples from a work piece such as a semiconductor wafer by first inserting the wafer in a Focused Ion Beam apparatus (FIB). A wedge or lamella of material is formed by milling a trench with a focused ion beam and then separating the wedge or lamella from the work piece. This wedge or lamella, with a thickness in excess of the desired thickness of e.g. 50 nm, is attached to a manipulator prior to the separation with e.g. ion beam induced deposition (IBID). A part of the wedge or lamella is then machined to a membrane with the desired thickness by milling with the focused ion beam, thereby forming the sample.

Although not disclosed in said U.S. patent, it is well known to the person skilled in the art to transport the thus formed sample, attached to the manipulator, to a TEM grid, attach the sample to the TEM grid and separate the sample from the manipulator by cutting it free from the manipulator with the ion beam. The sample, mounted on the TEM grid, is then taken from the ion beam instrument and transferred to a TEM for inspection.

The method is also known from U.S. Pat. No. 7,002,152. This patent discloses forming a sample by alternating exposure of opposite sides of a sample to a glancing ion beam. Here the work piece is not a wafer, but a lamella to be thinned. The use of a glancing ion beam minimizes e.g. crystallographic damage and the implantation of ions from the ion beam into the sample.

It is noted that the work piece may comprise or consist of semiconductor material, as is the case when machining a semiconductor wafer, but may also comprise or consist of other material, such as organic tissue in the form of a bacterium or a cell, a pharmaceutical composition, a polymer or a metallic sample.

A disadvantage of the known methods is that the finished sample, when transferring it from the FIB to the TEM, is exposed to air. The exposure to air may results in chemical changes of the surface of the sample, such as immediate oxidation. Such chemical changes have a negative impact on the quality of the samples, and may even render the sample unfit for subsequent inspection. In this context the quality of the sample is a measure of the condition of the sample during inspection to provide information of the sample in pristine condition (or to restore said information) when inspecting the sample.

A similar deterioration of the sample occurs when the sample is stored for a prolonged period for e.g. future investigation or comparison.

It is even known that a similar deterioration may occur when exposing the sample to the low pressures used in such a FIB for a prolonged time, as some residual oxygen or water is present, causing a slow oxidation of the sample.

A known partial solution to the problem is to transport and/or store the sample in an inert environment, such as in an evacuated transport unit or in a transport unit filled with an inert gas.

A problem to this partial solution is that even at a low (partial) pressure of e.g. oxygen or water oxidation may occur, and thereby the storage or transport of samples by this method does not reliably result in high quality samples. Also the costs associated with this partial solution, including the addition of a vacuum tight interface between the transport unit and the FIB and/or TEM, results in complex and expensive adaptations of the instruments used.

There is a need for a sample preparation method in which the sample is not deteriorated when taken from the particle-optical apparatus used for machining the work piece.

BRIEF SUMMARY OF THE INVENTION

The invention relates to a method for producing high-quality samples for e.g. TEM inspection. When thinning samples with e.g. a Focused Ion Beam apparatus (FIB), the sample often oxidizes when taken from the FIB due to the exposure to air. This results in low-quality samples, that may be unfit for further analysis. By forming a passivation layer, preferably a hydrogen passivation layer, on the sample in situ, that is: before taking the sample from the FIB, high quality TEM samples can be produced.

BRIEF DESCRIPTION OF THE DRAWINGS

The invention is now elucidated on the hand of figures. To this end:
FIGS. $1^a$, $1^b$ and $1^c$ schematically show the formation of a thinned lamella for inspection in a TEM.

DETAILED DESCRIPTION OF THE DRAWINGS

Figure 1A:
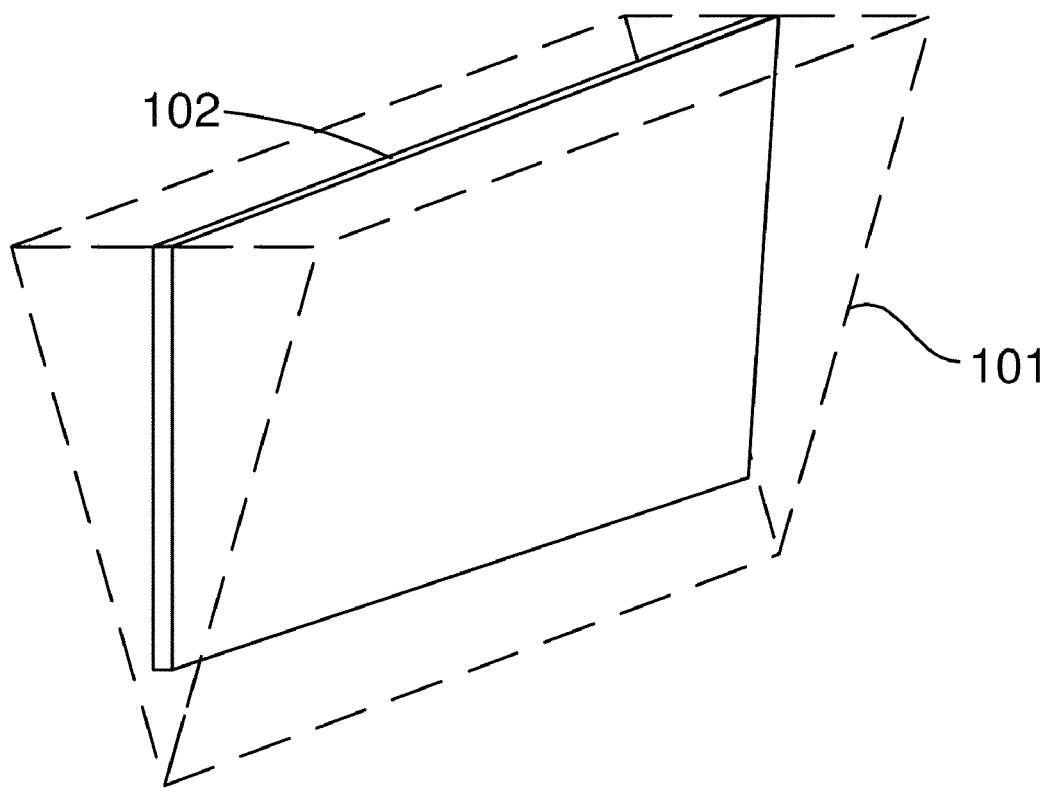
Figure 1B:
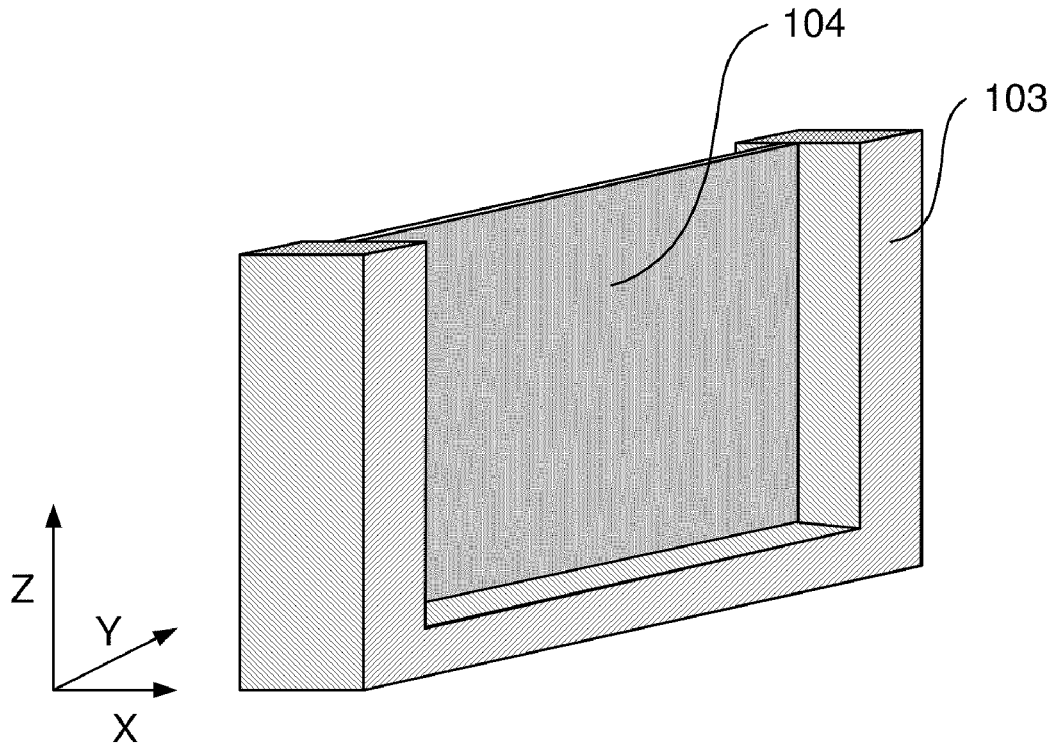
Figure 1C:
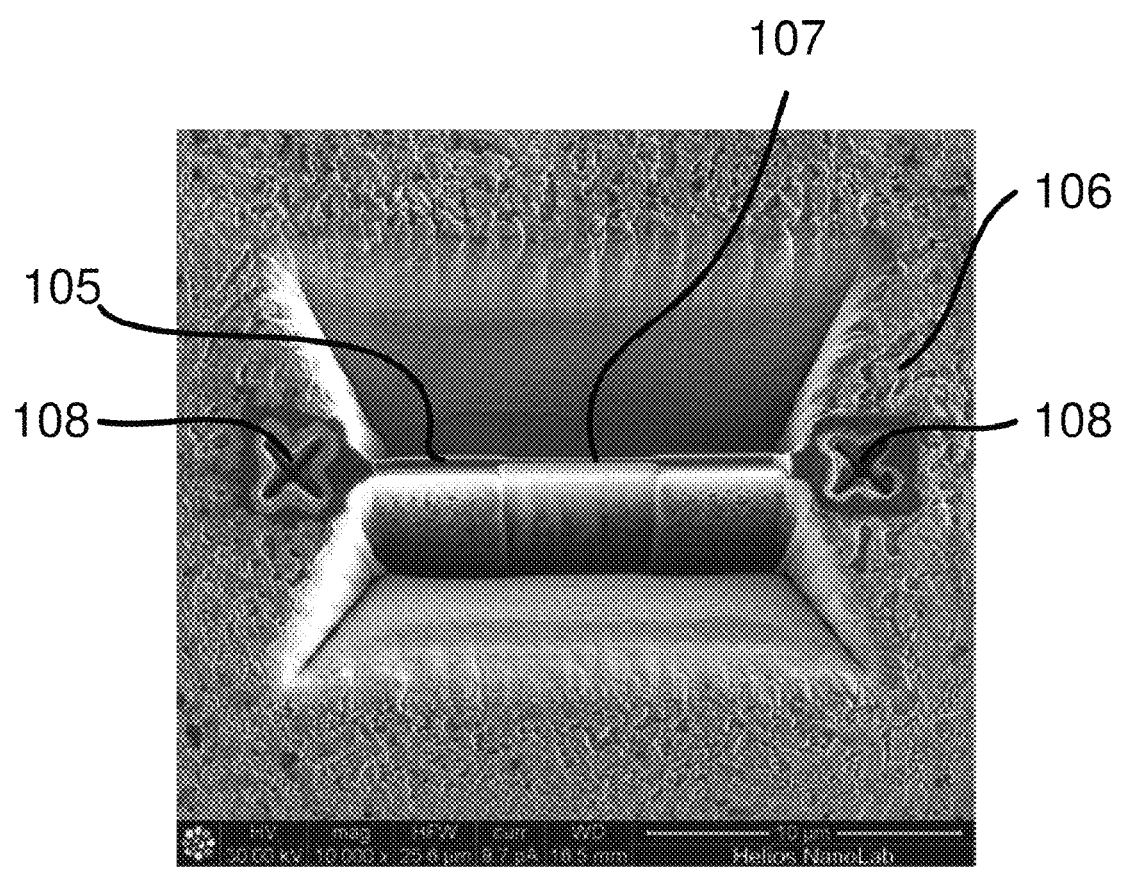

The method according to the invention is characterized in that a passivation layer is formed on the sample before the sample is removed from the particle-optical apparatus and the passivation layer is not an oxide layer.

Inventors observed that passivated TEM samples, using e.g. hydrogen passivation, were stable in time. The passivation was applied to the sample after thinning the sample by exposing the sample to wet chemical etching. The thinning may be the result of wet chemical etching, or may be the result of milling/etching with a FIB. Although such samples are stable in time, the quality of the samples differed. Inventors realized that this was due to e.g. oxidation of the sample before passivation, resulting in a change of the pristine samples before they could be protected by passivation. Applying the protective layer before such change can take place, that is: before exposing the sample to air, results in a high quality sample that is stable in time. Applying the protective passivation layer to the sample before exposing it to air is realized by applying the passivation layer in-situ in the instrument where the machining takes place. As known to the person skilled in the art such instruments machine the sample in an evacuated condition.

Inventors found that passivation not only resulted in TEM samples with improved quality, but that also samples used for e.g. Electron Back Scattered Patterning (EBSP) prepared with a FIB showed improved quality, resulting in e.g. better detection of Kikuchi lines. It is noted that EBSP samples are not thinned, but FIB preparation is used to obtain a smoothened and cleaned surface.

In an embodiment of the method according to the invention the passivation layer is formed by exposing the sample to ions and/or radicals formed in a plasma.

Exposing e.g. a semiconductor surface to a plasma is a well known method for forming a passivation layer. In this way it is known to form e.g. hydrogen passivation layers using a hydrogen bearing plasma or nitrogen passivation layers using a nitrogen bearing plasma.

It is noted that forming a plasma in a volume removed from the sample, and 'bleeding' reactive species (such as atomic hydrogen, atomic radicals and molecular radicals) to the sample while preventing ions to reach the sample and/or work piece, is known from e.g. U.S. Pat. No. 5,312,519. In this way a sample may be passivated without exposing the work piece directly to the plasma.

In another embodiment of the method according to the invention the passivation layer is formed by exposing the sample to a gas admitted by a gas injector.

As known to the person skilled in the art a Gas Injection System (GIS) is used in many FIB's to admit gasses to the chamber where a sample resides. Typically admission of gas is used for enhanced etching of the sample or depositing material on the sample. By admitting a proper gas to the sample, at the proper moment, a passivation layer is applied to the sample.

In yet another embodiment of the method according to the invention the passivation layer is a hydrogen passivation layer.

When using a hydrogen passivation layer for a TEM sample, one is further assured that the imaging of the sample is influenced as little as possible by the hydrogen, because hydrogen is a very light material, hardly interacting with the electron beam used by the TEM.

In a further embodiment of the method according to the invention the passivation layer is formed by exposing the sample to a gas comprising hydrogen, said gas decomposing when irradiated by a beam of charged particles.

By supplying a hydrogen bearing gas, such as $NH_3$, to the sample, preferably via a GIS, the gas adheres to the sample. By decomposing said gas with a charged particle beam, the sample is exposed to reactive hydrogen ions and/or radicals, resulting in the formation of a hydrogen passivation layer.

It is noted that hydrocarbons, although comprising hydrogen, may not result in a passivation layer due to the formation of a (non-volatile) carbon layer. Similar concurrent processes disabling the formation of a passivation layer may occur when using other gasses.

In a still further embodiment of the method according to the invention the beam of charged particles decomposing the gas is the focused particle beam.

Decomposition of gas by an ion beam is well known. By using the same ion beam for milling and for decomposing the gas used for the passivation, a relative simple apparatus can be used.

It is noted that the milling can be enhanced by admission of a gas as well. The apparatus may thus be used in a process where during milling an etch enhancement gas is used and thereafter another gas for the passivation.

In another embodiment of the method according to the invention the beam of charged particles is an electron beam.

Also known is the decomposition of a gas by electrons. This need not be a focused beam, but may be a beam of electrons from a so-named flood gun.

FIGS. $1^a$, $1^b$ and $1^c$ schematically show the formation of a thinned lamella for inspection in a TEM, FIG. $1^a$ schematically shows a wedge and lamella taken from a work piece. A wedge 101 of e.g. semiconductor material is freed from a work piece, e.g. a wafer. This wedge is then thinned to a lamella 102. This lamella often is still too thick for use as a TEM sample.

It is noted that the wedge may take the form of a thick lamella.

FIG. $1^b$ schematically shows that the earlier separated thick lamella 102 is locally thinned, so that a sample is formed with a relatively robust rim 103 and a thin membrane 104. Membrane 104 typically has a final thickness of less than 50 nm, although membranes with a thickness of e.g. 100 nm or more may be used for certain applications.

Milling is preferably done with an ion beam scanned over the surface of the lamella at a glancing angle, that is: with a direction parallel to or close to the Z-axis. Subsequent inspection in a TEM is preferably done with an electron beam impinging perpendicular to the membrane 104, that is: parallel to or close to the X-axis.

It is noted that this thinning may be done while the thick lamella is still connected to the work piece, but typically the final thinning is done while the lamella is separated from the work piece.

FIG. $1^c$ shows a photo of a lamella being cut from a work piece.

In this photo a sample 105 in the form of a lamella is formed and locally thinned while still connected to the work piece in the form of a wafer 106. The locally thinned membrane 107 in this photograph has a thickness of less than 100 nm.

The work piece shows two crosses 108 used in the automated milling process. Later in the process the lamella is freed from the work piece and therewith forms the TEM sample. Before freeing the sample from the work piece the lamella may be connected to a manipulator, as described in U.S. Pat. No. 5,270,552 to Hitachi, or the sample may be connected to a manipulator after separating the sample from the work piece, as described in U.S. Pat. No. 6,570,170 to Omniprobe.

It is noted that in this example the sample is thinned to its final thickness while attached to the work piece, but that it also known to machine the sample to its final thickness after excising it from the work piece. This final machining may take place in the same instrument (without exposing the unfinished sample to atmosphere), but may also be done in another apparatus. In the latter case the unfinished sample may be exposed to air, resulting in e.g. oxidation of the surface of the sample. However, as this surface layer is removed during the final machining, this need not lead to a lower of the quality of the sample after the final machining.

Figure 2:
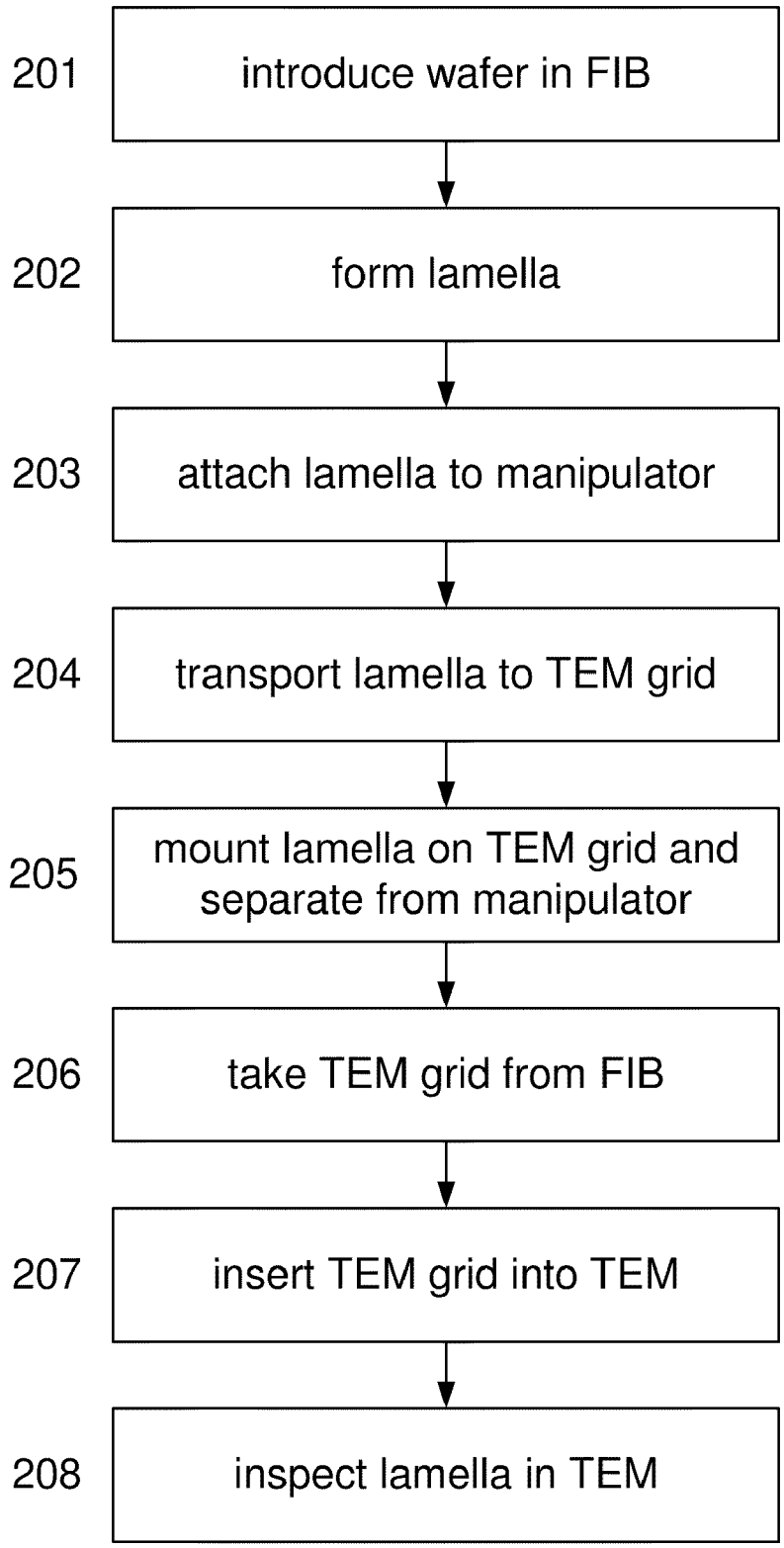
FIG. 2 shows a (prior art) method of forming a sample.

FIG. 2 schematically shows a prior art method of forming a sample.

In step 201 a work piece, such as a wafer, is introduced in the vacuum chamber of a FIB. This is normally done by mounting the wafer on a X-Y stage in the vacuum chamber. The wafer may be introduced via an airlock, and then positioned on the stage, or the vacuum chamber may be vented and opened so as to mount the wafer on the stage.

In step 202 a lamella is formed. Using a focused ion beam a wedge or lamella is excised from the work piece. The focused ion beam mills the surface. The milling may be enhanced by the introduction of proper etch enhancing gasses. The wedge or lamella is at least locally thinned to a thickness of typically 50 nm or less. As noted earlier, this final thinning may be done while the lamella is connected to the wafer, but it may be done while the lamella is removed from the sample.

It is noted that, as known to the person skilled in the art, the thickness of the sample can be deduced from the transparency of the sample for electrons. For this use, as well as for observing the progress of the milling, the method is preferably performed on an apparatus with a focused ion beam and a focused electron beam, so a combination of a FIB and a Scanning Electron Microscope (SEM). Such instruments are commercially available under the name DualBeam™ from FEI Company, Hillsboro, USA.

In step 203 the lamella is attached to a manipulator and freeing it from the work piece so as to transport the lamella when freed from the work piece. The manipulator typically comprises a needle to which the lamella may be attached, but manipulators of other form are known.

It is noted that attaching the lamella can take place before freeing it from the work piece (as described in U.S. Pat. No. 5,270,552), or can take place after freeing it from the work piece (as described in U.S. Pat. No. 6,570,170).

Attaching the lamella to the manipulator may comprise Ion Beam Induced Deposition (IBID), Electron Beam Induced Deposition (EBID), the use of electrostatic force, mechanical gripping, gluing, bonding by freezing, etc.

It is further noted that step 203 and step 202 can overlap in that the final thinning of the lamella can take place after freeing the lamella from the wafer.

In step 204 the lamella is transported to a TEM grid.

In step 205 the lamella is attached to the TEM grid, after which the lamella is separated from the manipulator. Separating the lamella from the manipulator may e.g. include cutting with an ion beam.

In step 206 the TEM grid is taken from the FIB. This may take the form of venting the vacuum chamber, and taking the TEM grid with e.g. tweezers, or it may involve passing the grid through an airlock. However, in both cases the TEM grid and the lamella are exposed to air, and oxides may form on the surface of the lamella. As the lamella is extremely thin, this may result in oxidation of most of the lamella, resulting in corruption of most of the structure of the lamella.

It is noted that it is known to transport samples in an air-tight box with inert gas, or in an evacuated box. The residual oxygen or water in such an enclosure often results in oxidation. Also the long time storage of samples for future reference using such boxes is impractical. Last, but not least, the interface between FIB and box, and between box and TEM, necessitate expensive adaptations prone to malfunction.

In step 207 the TEM grid is inserted in a TEM, typically by mounting it in a TEM sample holder.

In step 208 the sample is finally inspected in the TEM. The inspection may include imaging of the electron beam transmitted through the sample, determining energy losses of the transmitted electrons, detecting diffractograms, detecting secondary electrons, back-scattered electrons, X-rays, and/or e.g. light generated in the sample as a result of the irradiation with the electron beam, etc.

The invention involves forming a passivation layer before step 206 so as to protect the sample from oxidation in step 206 and following handling. Preferably this step is done between steps 203 and 204, or between steps 202 and 203. The passivation is preferably a hydrogen passivation, as a hydrogen passivation interferes with the inspection as little as possible, but other types of passivation are envisioned.

It is noted that although the method is described for and especially suited for forming samples for a TEM, also other inspection techniques using other instruments may benefit from the method according to the invention. Such a technique is the earlier mentioned preparation of EBSP samples.

It is noted that inventors observed that EBSP samples prepared with a FIB and analysed in-situ with EBSP (so: without exposing the sample to atmosphere), may deteriorate due to e.g. slow oxidation caused by residual gasses in the apparatus. This occurs e.g. when analysing titanium samples, titanium being a very reactive material. Therefore passivation may be preferred when analysing a EBSP sample in-situ or ex-situ.

We claim as follows:

1. Method of machining a work piece with a focused particle beam to form a sample, comprising:
    inserting the work piece in a particle-optical apparatus,
    machining the work piece to form the sample by exposing the work piece to a focused particle beam, and
    removing the sample from the particle-optical apparatus, characterized in that
    a passivation layer is formed on the sample after final machining of the sample and before the sample is removed from the particle-optical apparatus and
    the passivation layer is not an oxide layer.

2. The method of claim 1 in which the passivation layer is formed by exposing the sample to ions formed in a plasma, radicals formed in a plasma, or both ions and radicals formed in a plasma.

3. The method of claim 1 in which the passivation layer is formed by exposing the sample to a gas admitted by a gas injector.

4. The method according to claim 1 in which the passivation layer comprises a hydrogen passivation layer.

5. The method of claim 4 in which the passivation layer is formed by exposure to a gas comprising hydrogen, said gas decomposing when irradiated by a beam of charged particles.

6. The method of claim 5 in which the beam of charged particles comprises the focused particle beam.

7. The method of claim 5 in which the beam of charged particles comprises an electron beam.

8. The method of claim 1 in which the sample comprises titanium.

9. A method of preparing a sample from a work piece:
    directing a charged particle beam toward the work piece in a vacuum chamber to form a sample from the work piece; and
    forming a passivation layer that is not an oxide layer on the sample before removal of the sample from the vacuum chamber and after final machining of the sample.

10. The method of claim 9 further comprising thinning at least a portion of the sample to a thickness of less than 100 nm.

11. The method of claim 9 further comprising viewing the sample using a transmission electron microscope.

12. The method of claim 9 further comprising mounting the sample in a TEM grid.

13. The method of claim 9 further comprising observing the sample in situ with electron back scattered patterning.

14. The method of claim 9 in which forming the passivation layer comprises exposing the sample to ions formed in a plasma, radicals formed in a plasma, or both ions and radicals formed in a plasma.

15. The method of claim 9 in which forming the passivation layer comprises exposing the sample to a gas admitted by a gas injector into the vacuum chamber containing the sample.

16. The method of claim 9 in which forming the passivation layer comprises forming a hydrogen passivation layer.

17. The method of claim 9 in which forming the passivation layer comprises forming a nitrogen passivation layer.

18. The method of claim 9 in which forming the passivation layer comprises decomposing a gas using a charged particle beam.

19. The method of claim 9 in which forming a passivation comprises decomposing $NH_3$ using a charged particle beam.

20. The method of claim 9 in which forming a passivation comprises decomposing a gas using an electrons from an electron flood gun.

21. The method of claim 9 in which directing a charged particle beam toward the work piece in a vacuum chamber to form a sample from the work piece includes thinning a wedge-shaped sample from the work piece before forming the passivation layer.

22. The method of claim 9 in which the sample is thinned before the sample is freed from the work piece.

23. The method of claim 9 in which the sample is thinned after the sample is freed from the work piece.

24. Method of machining a work piece with a focused ion beam to form a lamella, comprising:
   inserting the work piece in a particle-optical apparatus,
   machining the work piece to form the lamella by exposing the work piece to a focused ion beam,
   thinning the lamella such that the lamella is capable of being observed under a Transmission Electron Microscope,
   forming a passivation layer on the lamella after the final thinning of the lamella, said passivation layer not being an oxide layer,
   removing the lamella from the particle-optical apparatus after forming the passivation layer.

* * * * *